(12) United States Patent
Souter

(10) Patent No.: US 7,815,605 B2
(45) Date of Patent: Oct. 19, 2010

(54) EMERGENCY MEDICATION PUMP INJECTION SYSTEM

(76) Inventor: Steve R. Souter, 10255 S. Loridan, Sandy, UT (US) 84092

( * ) Notice: Subject to any disclaimer, the term of this patent is extended or adjusted under 35 U.S.C. 154(b) by 136 days.

(21) Appl. No.: 11/946,740

(22) Filed: Nov. 28, 2007

(65) Prior Publication Data
US 2009/0137956 A1 May 28, 2009

(51) Int. Cl.
*A61M 1/00* (2006.01)
*A61M 5/00* (2006.01)

(52) U.S. Cl. .................... 604/151; 604/246

(58) Field of Classification Search .......... 604/151
See application file for complete search history.

(56) References Cited

U.S. PATENT DOCUMENTS

| | | | |
|---|---|---|---|
| 4,559,036 A | 12/1985 | Wunsch | |
| 4,696,671 A * | 9/1987 | Epstein et al. | 604/67 |
| 4,705,506 A | 11/1987 | Archibald | |
| 4,756,706 A | 7/1988 | Kerns et al. | |
| 4,828,545 A | 5/1989 | Epstein | |
| 4,878,896 A | 11/1989 | Garrison et al. | |
| 4,898,578 A | 2/1990 | Rubalcaba, Jr. | |
| 4,900,305 A | 2/1990 | Smith et al. | |
| 4,925,444 A | 5/1990 | Orkin et al. | |
| 5,041,086 A | 8/1991 | Koenig et al. | |
| 5,057,076 A | 10/1991 | Polaschegg | |
| 5,207,642 A | 5/1993 | Orkin et al. | |
| 5,221,268 A | 6/1993 | Barton et al. | |
| 5,298,021 A | 3/1994 | Sherer | |
| 5,304,126 A | 4/1994 | Epstein et al. | |
| 5,378,231 A | 1/1995 | Johnson et al. | |
| 5,431,627 A * | 7/1995 | Pastrone et al. | 604/65 |
| 5,527,289 A | 6/1996 | Foster et al. | |
| 5,531,697 A | 7/1996 | Olsen et al. | |
| 5,547,470 A | 8/1996 | Johnson et al. | |
| 5,609,575 A | 3/1997 | Larson et al. | |

(Continued)

FOREIGN PATENT DOCUMENTS

JP 2005-334113 12/2005

OTHER PUBLICATIONS

Baxter U.S.—Colleague Volumetric Infusion Pumps, Retrieved May 16, 2007, from the world wide web at http://www.baxter.com/products/medication_management/infusion_pumps/colleague/index.html.

(Continued)

*Primary Examiner*—Nicholas D Lucchesi
*Assistant Examiner*—Jason Flick
(74) *Attorney, Agent, or Firm*—Workman Nydegger

(57) ABSTRACT

An emergency multi-medication pump injection system is designed for use in rapidly and automatically calculating and administering multiple medications in an emergency setting. The system includes a compact, portable housing comprising a plurality of medication ports, each port configured to receive a corresponding ampoule containing a corresponding medication. The system further includes at least one pump on or within the housing for dispensing a calculated dosage amount of one or more medications from the ampoules, at least one delivery tube for conveying the medication(s) from the system for delivery to the patient, and safety means for ensuring that each ampoule can only be installed in a port to which the particular ampoule corresponds. The pump injection system may include data inputs for inputting data relating to patient weight, medication concentration, medication dosage, and the like.

25 Claims, 4 Drawing Sheets

U.S. PATENT DOCUMENTS

| | | | |
|---|---|---|---|
| 5,681,285 A | 10/1997 | Ford et al. | |
| 5,772,635 A * | 6/1998 | Dastur et al. | 604/131 |
| 5,925,014 A | 7/1999 | Teeple, Jr. | |
| 6,117,103 A | 9/2000 | Tverskoy et al. | |
| 6,123,686 A | 9/2000 | Olsen et al. | |
| 6,132,416 A * | 10/2000 | Broselow | 604/506 |
| 6,146,360 A | 11/2000 | Rogers et al. | |
| 6,355,019 B1 * | 3/2002 | Kriesel et al. | 604/132 |
| 2001/0025156 A1 | 9/2001 | Bui et al. | |
| 2003/0051737 A1 | 3/2003 | Hickle et al. | |
| 2004/0015123 A1 * | 1/2004 | Smith et al. | 604/65 |
| 2005/0277912 A1 | 12/2005 | John | |
| 2006/0009734 A1 | 1/2006 | Martin | |
| 2007/0135765 A1 * | 6/2007 | Miller et al. | 604/131 |
| 2007/0197978 A1 * | 8/2007 | Wortham | 604/246 |

OTHER PUBLICATIONS

Sigma-Smart Infusion Pumps, Retrieved May 16, 2007, from the world wide web at http://www.sigmapumps.com.

* cited by examiner

EMERGENCY MEDICATION PUMP INJECTION SYSTEM

BACKGROUND OF THE INVENTION

1. The Field of the Invention

The present invention is directed to the field of emergency medicine. More particularly, the present invention is directed to an emergency medication pump system designed to automatically calculate dosages and administer selected medications to a patient based on minimal input (e.g., the patient's weight).

2. The Relevant Technology

The intravenous infusion of various types of medications is an important part of the treatment of many patients. This is particularly true in an emergency situation where a patient may require a series of life-saving injections of a variety of medications. Often these injections must be given in rapid succession and according to a particular protocol. Delays and/or deviations from protocol can be life-threatening. Injections of medications may begin when a patient is first contacted by emergency medical technicians or when the patient arrives in the emergency department of a hospital. Regardless, when a patient is first administered to by emergency medical personnel, the personnel will rapidly assess the patient's clinical situation and, if appropriate, they may immediately begin giving intravenous medications.

For example, if an unconscious patient arrives in the emergency department with severe breathing difficulties, it is typically necessary to insert a breathing tube into the patient's airway for ventilation and oxygenation. This process is called emergency endotracheal intubation. Intubation, however, must be performed with care because of the patient's innate gag reflex. For example, if the breathing tube is inserted into the patient's airway without pretreating the patient with proper medications there is a considerable risk that the patient may vomit and choke.

Typically, emergency endotracheal intubation is performed in conjunction with a procedure called rapid sequence intubation ("RSI"). RSI is the process of inducing unconsciousness and motor paralysis prior to emergency endotracheal intubation. When a patient needing intubation arrives in the emergency department, the team of nurses and physicians immediately begin giving intravenous fluids, begin oxygen by bag mask ventilation, and arrange equipment and medications to perform RSI. Typical dosages are based on an estimate of the patient's weight and on the specific clinical situation. Of course, those of skill in the art will recognize that the term "patient weight" as used herein refers to not necessarily the actual weight of the patient, but an ideal body weight, as excess body fat is typically not accounted for when determining dosing of most medications (e.g., a typical adult patient may have a "weight" of about 70 kg).

A patient needing RSI will receive a potent induction agent to induce anesthesia, followed by a rapid acting neuromuscular blocking agent to induce partial paralysis. A typical induction agent is Etomidate, given at a rate of 0.3 mg/kg, and a typical blocking agent succinylcholine, given at a rate of 1.5 mg/kg. In some situations the patient may also receive so-called "pre-medications" prior to administering the induction agent and the blocking agent. These pre-medications may be administered to protect the central nervous system in patients who are being intubated where a brain injury, such as an intracranial hemorrhage, is suspected. For example, a patient may receive Fentanyl at a rate of 3 μg/kg, Lidocaine at a rate of 1 mg/kg, and/or a defasciculating dose of Vecuronium.

Another example of an emergency medical procedure involving rapid and successive injection of multiple medications is advanced cardiac life support ("ACLS"). ACLS is a comprehensive approach to the resuscitation and/or treatment of a patient with a serious heart condition. Typical medications used in ACLS include epinephrine, atropine, dopamine, lidocaine, and anti-arrhythmics. ACLS is used by emergency medical personnel to restore normal cardiac function to patients in cases of cardiac arrest. Cardiac arrest is a general term that includes asystole, bradycardia, ventricular tachycardia, and pulseless electrical activity (PEA).

ACLS is used in most cases of general cardiac arrest; however, the precise treatment that a patient receives is a function of the patient's condition. For example, in a case of asystole where the patient has no pulse and there is an absence of electrical activity in the heart, emergency medical personnel will perform cardiopulmonary resuscitation along with administering injections of epinephrine at a rate of 0.01-0.03 mg/kg followed by atropine at a rate of 0.02 mg/kg. In a case of bradycardia where the patient's heart rate is slower than expected for a given situation, emergency medical personnel will administer injections of atropine at a rate of 0.02 mg/kg followed by epinephrine at a rate of 0.01-0.03 mg/kg along with electrical stimulation of the heart. Other medications may be given in different situations. In addition, patients undergoing ACLS may also be candidates for RSI.

A third example of an emergency medical procedure involving rapid and successive injection of multiple medications is procedural sedation. Procedural sedation is a clinical technique that creates a decreased level of awareness for a patient during a potentially painful and/or frightening procedure yet maintains protective airway reflexes and adequate spontaneous ventilation. Agents used in procedural sedation are of three general classes: sedatives, analgesics, and induction agents in reduced amounts. For example, if a patient comes into the emergency department with a dislocated shoulder, it is generally necessary to sedate the patient in order to return the head of the humerus bone to its place in the shoulder joint in a procedure called "reduction" or "reducing the shoulder." Shoulder dislocation causes the patient great pain, and the subsequent reduction can be excruciating in and of itself. As a result of the muscle tension that naturally results from the pain of a dislocated shoulder, great strength is required to reduce the shoulder if the patient is not relaxed and sedated. In contrast, under sedation the patient is much more comfortable and the reduction can be performed with a minimum of effort. In a typical protocol, the patient is preoxygenated and intravenous Propofol is administered in 20 mg increments up to a maximum dosage of about 1.5-3.0 mg/kg. The Propofol injections are repeated until the patient is relaxed and the shoulder can easily be reduced back into place by the physician.

A common thread that joins RSI, ACLS, procedural sedation, and other emergency procedures under current practice is that each medication administered to a patient requires a separate calculation to arrive at a correct dosage based mainly or exclusively on the patient's weight. Time is of the essence in emergency medicine, and these calculations cost valuable time. Currently the solution to this need is to have the multiple medications necessary assembled in a single box which is carried to the bedside of the patient in distress. Some facilities place a locked box in the trauma/resuscitation rooms that are stocked with these medications, and the box is opened as the patient arrives. The physician calculates the amount of each medication to be administered. The process is repeated for as many as 5 (or more) medications. The physician gives orders to a nurse to draw into separate syringes the medications to be utilized based on the patient's weight and clinical situation. Valuable time is spent drawing each medication into a separate syringe. If the syringes are placed at the patient's bedside, they can be indistinguishable from the other syringes now full of clear liquid, making a mix-up possible.

At the physician's order, the medications are injected into the IV rapidly in a set order. More time is expended as each syringe is injected serially into the IV port. The nurse handling the medications is typically a more senior, experienced member of the team. Larger facilities may even call a pharmacist to the Emergency Department to prepare these medications. The team waits for this process to be completed when time is of the essence. The mental concentration required for calculating, confirming accuracy, and overseeing administration of these medications distracts or delays the physician and other members of the team from performing other life saving interventions. As noted, the more experienced members of the medical team are involved in these crucial steps. Freeing them to focus their efforts elsewhere would be invaluable.

In addition to wasting valuable time and resources, the current procedure increases the risk of errors in dosing, and presents a risk of accidental needle sticks to the emergency medical personnel due to the rush in providing treatment to the patient in the emergency situation. Moreover, most medications are clear liquids and they cannot easily be differentiated once they are drawn into a syringe. Because of this, medications can be given in the wrong sequence if they are drawn into a series of syringes and laid out for injection. Further, because of the rush that is natural to an emergency situation, records of which medications were administered, when they were administered, and in what amounts may not be properly kept or correctly remembered afterwards.

Accordingly, there are a number of difficulties associated with emergency medicine where it is necessary to rapidly deliver multiple injections of multiple medications. In particular, there are a number of difficulties present in terms of locating the appropriate medications, calculating correct dosages, drawing up the medications into a series of syringes, and administering them to the patient in the proper sequence. Therefore, it would be advantageous to provide a system where the medications for a number of emergency procedures are preassembled where the various medications can be administered without having to manually calculate dosage amounts for each, and where they can be rapidly administered in the proper sequence, all while minimizing the disadvantages described above.

BRIEF SUMMARY OF THE INVENTION

The present invention is directed to emergency medication pump systems configured for use in rapidly calculating and administering correct dosages of multiple medications in an emergency setting. The system may include, for example, a plurality of medications pre-installed in the pump system. The system provides the ability to automatically administer clinically correct dosages of all of the medications installed in the pump system, or a selected subset thereof with minimal input (e.g., patient weight) from a doctor, nurse, or other emergency medical provider. The system is advantageously small, portable, and compact so as to be easily carried by a nurse to the bedside, or from a helicopter or ambulance to the side of a critically ill or injured patient.

The system provides for immediate intervention in managing a critically ill or injured patient (e.g., patient's in respiratory distress, cardiac arrest or for procedural sedation). The system is advantageously designed to accurately calculate and intravenously deliver potent pharmacologic agents commonly used in such situations. Preferably, only the patient's weight is entered and the system automatically calculates the appropriate dose for delivery to that patient. Dosing to pediatric patients may be based on the patient's length (which is correlated to weight). The Broselow tape is universally recognized for this purpose. The Broselow tape also assigns a color to each length (and correlated weight) range. Colors assigned to each length (and correlated weight) range of a pediatric patient may also be coded into the system so that the practitioner has only to select the appropriate color (which signifies the corresponding length and weight).

The multi-medication pump injection system includes a compact, portable-sized housing with a plurality of medication ports. In turn, each of the plurality of medication ports is configured to receive a corresponding medication ampoule containing a corresponding medication. That is, each port is configured to receive one and only one type of medication ampoule containing one and only one type of medication. This prevents inadvertently administering the wrong type of medication. For example, the ampoules may be uniquely colored, shaped, and/or sized to be placed in a pump receptable port identical in color and having a corresponding shape and/or size.

The emergency medication pump system includes safety means for ensuring that each ampoule can only be installed in the port to which the ampoule corresponds. In one embodiment, the safety means may be configured as a mechanical interlocking structure system wherein each of the plurality of ports is equipped with a specific arrangement of keyways, e.g., tabs and/or channel-shaped structures, and each type of ampoule is equipped with a complementary arrangement of mechanical structures. When an ampoule is installed in the port to which it corresponds, the safety interlocking structures of the ampoule mate with the complementary structures of the port. As such, a given ampoule cannot be installed in a medication port to which it does not correspond.

In another embodiment, the safety means may include a color matching system wherein each port is designated by a specific color, and each type of medication ampoule is also designated with a specific matching identical color. In other words, the colors designating the port and the medication ampoule type match (i.e., they are the same) when an ampoule is inserted into the port to which it corresponds.

In another embodiment, the safety means may include a name matching system wherein the name of the medication corresponding to a port is clearly printed in large letters on both the port and on the medication ampoule itself.

In another embodiment, the safety means may include sizing each ampoule differently. For example, because different medications will be used up at different rates as the system is used multiple times, it would be advantageous to provide ampoules of different sizes such that the plurality of ampoules empty at about the same time (e.g., after about 1-4 dosages). Such a configuration further acts as safety means as the ampoules and ports are sized to receive one another, such that different sized ampoules prevents an ampoule from being inserted (or attempting to insert) the ampoule into the wrong port. One will appreciate, of course, that the system may preferably include more than one of the above described safety means. For example, the ampoules and ports may be uniquely colored, shaped, and sized to be placed in a pump receptable port identical in color and having a corresponding shape and size.

The system includes at least one pump disposed on or within the housing. The system may be configured with a single pump configured to dispense medication from all of the ampoules received within the housing, or the system may be configured with at least one pump corresponding to each ampoule. In either case, the system is programmed such that the pump or pumps dispense a calculated dosage amount of at least one medication from one or more of the plurality of medication ampoules received within the housing upon input provided by the user.

The system includes at least one delivery tube configured to transport medication from the one or more ampoules received in the system to a patient. In particular, the delivery tube has a distal end and at least one proximal end, wherein the at least one proximal end is either attached to one or more ampoules and/or to the pump(s) and the distal end is attached to the patient's IV line.

In one embodiment, the emergency medication pump system may include a key or other input interface for executing an injection sequence. For example, the input may comprise an inject key, button, or other interface. When the key is pressed, the injection sequence is executed, the pump or pumps are activated, and the medication is delivered to the patient through the delivery tube.

In one embodiment, the system may include a plurality of medication selection keys. While the medication pump system may include a variety of different medications, not all medications are needed in every situation. That is, the identity of the medications needed and the order in which they are to be given is a function of the clinical state of the patient. In this embodiment, the needed medications are selected by pressing the medication selection keys. According to one embodiment, the order in which the medications are dispensed may be determined by the order in which the keys are pressed.

In one embodiment, the emergency medication pump system is configured and/or programmed to administer one or more of a plurality of medications to a patient with minimal input from a doctor, nurse, or other emergency medical provider. Typically, the dosage amount for a given medication is based on the concentration of the medication (e.g., measured in mg/ml), the dosage rate of the medication (e.g., measured in mg/kg), and on the patient's weight (e.g., measured in kg). In one embodiment, the system may be pre-programmed with default values for the concentration and dosage rates for the plurality of medications installed in the system. In a related embodiment, the system may be programmed to dispense at least one medication installed in the system based only on input of a patient's weight. That is, if the concentrations of the medications installed in the system are within default values and if the clinical situation does not call for a deviation from the standard dose or order of administration, a patient's weight may be the only input necessary in order for the system to calculate and administer a dose for at least one of the medications installed in the system.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction and Definitions

Figure 1:
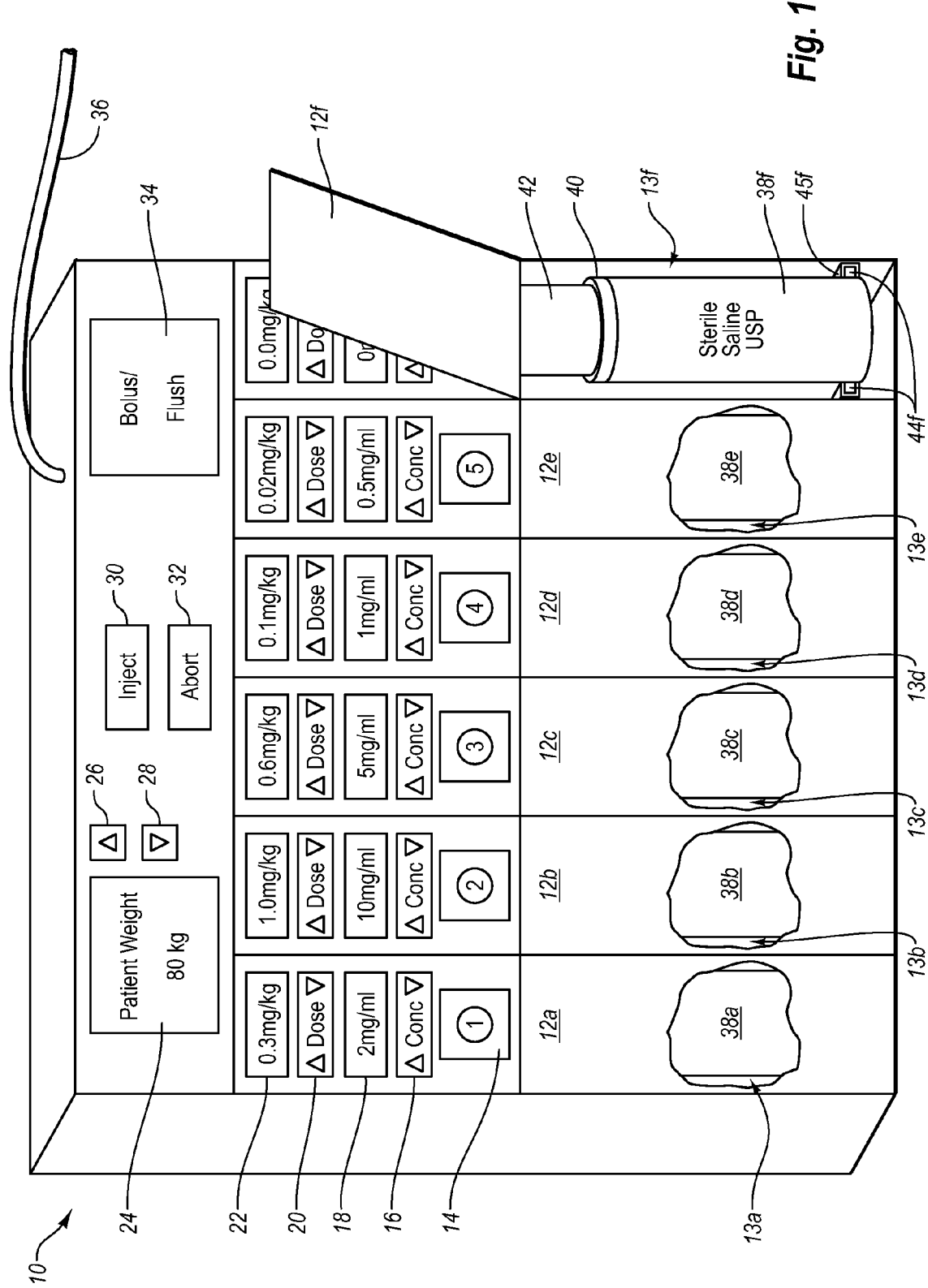
FIG. 1 illustrates a schematic view of an embodiment of a multi-medication pump injection system that includes ports for receiving a plurality of different medications.

The present invention extends to apparatuses, systems, and methods for automatically administering emergency medication to a patient in an emergency medical setting. In particular, the present invention is directed to emergency medication pump systems configured for use in automatically and rapidly calculating and administering multiple medications in an emergency setting. The system is advantageously designed to accurately calculate and intravenously deliver potent pharmacologic agents commonly used to administer to patients in respiratory distress and/or cardiac arrest, or for procedural sedation.

Advanced Cardiovasulcar Life Support (ACLS) is a comprehensive approach to the resuscitation or treatment of a patient with a serious heart condition (e.g., in cardiac arrest). Administration of multiple medications, given in specific doses calculated by patient weight is a critical part of ACLS. Rapid Sequence Intubation (RSI) is the administration of a potent induction agent followed immediately by a rapidly acting neuromuscular blocking agent to induce unconsciousness and motor paralysis for tracheal intubation (i.e., placement of a tube in the trachea for ventilation and oxygenation). Procedural sedation is helpful where it may be necessary to produce a decreased level of awareness within the patient during a painful or frightening procedure while maintaining protective airway reflexes and adequate spontaneous ventilation. An example would be a patient undergoing reduction of a dislocated shoulder. There are many different medications used in these scenarios. Under current practice, each medication requires separate calculations to arrive at the correct weight-based dose.

In a preferred embodiment, only the patient's weight (or a patient length and/or Broselow tape color corresponding to patient weight) is entered and the system automatically calculates the appropriate dose for delivery to that patient. Dosing to pediatric patients may be based on the patient's length (which is correlated to weight). The Broselow tape is universally recognized for this purpose. The Broselow tape also assigns a color to each length (and correlated weight) range. Colors assigned to each length (and correlated weight) range of a pediatric patient may also be coded into the system so that the practitioner has only to select the appropriate color (which signifies the corresponding length and weight). Use of the Broselow tape colors (e.g., coded into the system) is particularly helpful as many pediatric patients do not know their weight even if they were conscious, and estimating the weight of a pediatric patient is often slow and intimidating. While it may be fairly simple to estimate the ideal weight of a given adult within 10-20% for dosing needs (e.g., a average adult may have a dosing weight of about 70 kg) it is more difficult to accurately estimate weight of a child based simply on viewing the child. Furthermore, coding the Broselow colors into the system simplifies the work required of the practitioner as only the color need be selected as seen on the tape (when measuring the child); it is not necessary to then determine the correlated weight, as this information can be coded into the system. The following table shows the assigned color, the corresponding length, and the correlated weight.

| Color | Length | Weight |
| --- | --- | --- |
| Gray | 42.2-60.79 cm | 3-5 kg |
| Pink | 60.8-67.79 cm | 6-7 kg |
| Red | 67.8-75.29 cm | 8-9 kg |
| Purple | 75.3-85.09 cm | 10-11 kg |
| Yellow | 85.1-97.79 cm | 12-14 kg |
| White | 97.8-110.19 cm | 15-18 kg |
| Blue | 110.2-121.89 cm | 19-23 kg |
| Orange | 121.9-133.69 cm | 24-29 kg |
| Green | 133.7-146.59 cm | 30-36 kg |

The departments and/or environments that the emergency medication delivery system would be used in include the Emergency Department, hospitalized patients in the ICU, and/or on the floor. The system provides an ideal solution for stabilization and treatment of patients in the field by life flight (i.e., air transport) or paramedic teams prior to or during ground or air transport.

The system may include, for example, a plurality of medications pre-installed in the pump system. The system provides the ability to automatically administer clinically correct dosages of all of the medications installed in the pump system, or a selected subset thereof with minimal input (e.g., patient weight) from a doctor, nurse, or other emergency medical provider.

As used herein, the term "multi-medication pump injection system" generally refers to an assembly of mechanical components, microprocessor modules, and command and control systems configured to automatically and rapidly deliver medication to a patient, preferably with minimal input (e.g., only patient weight) from an emergency medical practitioner. The system includes a plurality of medication ports with each port configured to receive a corresponding medication ampoule containing a corresponding medication.

II. Exemplary Emergency Medication Delivery Systems

Along these lines, one will appreciate that at least one aspect of the present invention, therefore, is that the multi-medication pump injection system can be configured to include any number of medications typically used in an emergency setting. In particular, the multi-medication pump injection system can include configurations assembled to address specific medical situations, or the system could be relatively easily configured to include many if not all of the medications most commonly used in a variety of emergency medical situations. For example, separate systems could be configured for RSI, ACLS, and/or Procedural Sedation, or one system could be assembled with the medications needed for all three procedures.

In a typical scenario, the multi-medication pump system may be used to administer a plurality of medications to a patient in an emergency situation. In practice, the pump system may be used as follows: an emergency medical provider encounters a patient, the care provider assesses the patient's condition, the care provider immediately begins administering IV fluids to the patient, the care provider attaches the system to the patient's IV line, the care provider enters the patient's weight, the care provider decides which medications the patient needs from amongst those installed in the system, and finally the provider executes an inject command. The system may also be programmed or configured to tailor the dosage based on the patient's length and/or Broselow tape color. For example when the patient is a child, length may be used to estimate weight. The Broselow tape is a universally recognized tool correlating length (where different length ranges are correlated to a color) and weight for pediatric patients. As such, the system may be programmed to tailor the dosage based on the patient's Broselow tape color (e.g., the practitioner selects the color corresponding to the child patient's length).

Referring now to the Figures, FIG. 1 illustrates a schematic view of an embodiment of a multi-medication pump injection system 10 according to an embodiment of the present invention. As shown in FIG. 1, a multi-medication pump injection system 10 comprises a compact, portable housing. The housing of the system 10 can take a number of forms. As depicted in FIG. 1, the system 10 may comprise a substantially rectangular shaped box. Advantageously, the system 10 is configured with dimensions and weight making it both compact and portable. Preferably, the housing occupies a volume not greater than about 18 dm$^3$. For example, a rectangular box with dimensions of about 40 cm×about 30 cm×about 15 cm has a volume of about 18 dm$^3$. More preferably, the housing occupies a volume not greater than about 9 dm$^3$. For example, a rectangular box with dimensions of about 30 cm×about 30 cm×about 10 cm has a volume of about 9 dm$^3$. Most preferably, the housing occupies a volume of no more than about 6 dm$^3$. For example, a rectangular box with dimensions of about 30 cm×about 20 cm×about 10 cm has a volume of about 6 dm$^3$. In addition, the system 10 is advantageously configured to be relatively lightweight. Preferably, the system 10 is configured to weigh between about 1 and 5 kg. More preferably, the system 10 is configured to weigh between about 2 and about 4 kg. Most preferably, the system 10 is configured to weigh no more than about 3 kg.

As described above, the system 10 is advantageously configured with dimensions and weight making it both compact and portable. Providing a medication pumping system 10 that is lightweight and compact and therefore easy to stow and/or transport (e.g., in an ambulance, wall cabinet, and/or on a medical helicopter) is particularly desirable because the system 10 is intended for use both in the field, such as in an ambulance or a life-flight helicopter, and/or in a hospital emergency department. That is, the system is designed to be lightweight, compact and portable so as to be practical for use in the field or in a hospital emergency department, where the environment is often chaotic and emergency medical personnel need to be able to easily maneuver around the patient. Providing a system that is both lightweight and compact allows it to be easily taken into the field in an ambulance or life-flight helicopter where space is at a premium. Such would certainly not be the case with existing large and heavy pump assemblies which must be wheeled from room to room within a hospital, and which are simply not practical for use under emergency conditions. A system 10 having the above recited dimensions is lightweight, compact and portable, and well-suited to the requirements of emergency medicine.

In one embodiment, the system 10 may include a compact, portable housing with a plurality of medication ports 13a-13f. Each medication port is in turn configured to receive a corresponding medication ampoule containing a corresponding medication 38a-38f. For example, port 13f is configured to receive and couple with ampoule 38f, which in this example contains sterile saline solution. In other words, each medication port is configured to receive one and only one type of medication ampoule 38 containing one and only one type of medication. The system 10 may be configured to Opium include medication ports configured to receive ampoules containing, for example, Etomidate, Propofol, Ketamine, Midazolam, Lorazapam, Succinylcholine, Rocuronium, Vecuronium, Atropine, Fentanyl, Lidocaine, Epinephrine, sterile isotonic saline solution, sterile water, Ringer's solution, and/or other emergency medications and/or other IV medical fluids.

In one embodiment, each of the plurality of medication ports 13a-13f is covered by a corresponding door 12a-12f that can be selectively opened and closed as needed. When a door 12 is closed the door 12 conceals the corresponding medication port 13. When a door is open (e.g., door 12f), the medication port (e.g., port 13f) can be accessed.

In one embodiment, the system 10 may comprise a number of control, data input, and data readout mechanisms. For example, the system 10 may comprise a plurality of medication selection interfaces (e.g., key 14). In one embodiment, each medication selection key 14 is disposed adjacent to the corresponding medication port. While the system 10 may include a plurality of different medications, not every medication is needed in every situation. The medication selection keys 14 are configured to allow an emergency medical provider to select one or more medications for administration to a patient from amongst the plurality of medication ampoules 38 installed in the system 10.

In one embodiment, the medication selection keys 14 are additionally configured to control the order of dispensing of the medications from the ampoules 38 received in the system 10. If, for example, a user decides to administer medications 3, 5, and 2 to a patient in that order, the user can press the selection keys 14 corresponding to corresponding medication ports 13c, 13e, and 13b in that order. In such an example, when the medications are dispensed, they will be dispensed in the order that the keys 14 were pressed.

In one embodiment, the system 10 may include a plurality of concentration adjustment keys 16 disposed adjacent to the corresponding medication ports 13a-13f. The concentration adjustment keys 16 are configured to allow an emergency medical provider to adjust a concentration for at least one of the medications received in the system 10. The system 10 is typically programmed with default concentrations for the plurality of medications in the ampoules 38 received in the plurality of medication ports 13. If, however, the concentration in at least one of ampoules 38a-38f is different than at least one of the default values, the concentration adjustment keys 16 allow an emergency medical provider or other user to override the default concentration value and enter a new concentration value. Additionally, the system 10 includes a plurality of concentration readout displays 18 that readily allow an emergency medical provider or other user to see the concentration value that is input into the system 10 as either a default value or as a manually entered override value.

In one embodiment, the system 10 may include a plurality of dosage rate adjustment keys 20, each corresponding to a respective medication port 13. The dosage rate adjustment keys 20 are configured to allow an emergency medical provider to adjust a dosage rate for one or more of the medications installed in the system 10. The system 10 is typically programmed with default dosage rates for the plurality of medications in the ampoules 38a-38f received in the plurality of medication ports 13a-13f. If, however, a desired or proper dosage rate for at least one of medications in at least one of the ampoules 38a-38f is different than at least one of the default values, the dosage rate adjustment keys 20 allow an emergency medical provider or other user to override the default value and enter a new dosage rate. Additionally, the system 10 includes a plurality of dosage rate readout displays 22 that readily allow an emergency medical provider or other user to see the dosage rate value that is input into the system 10 as either a default value or as a manually entered override value.

In one embodiment, the system 10 may include a plurality of weight adjustment keys 26 and 28 configured to allow an emergency medical provider to enter a patient's weight or adjust up or down from a default setting (e.g., 70 kg). Typically, the dosage amount (i.e., the volume of medication solution administered to a patient) for each of the plurality of medications received in the system 10 is a function of the concentration of the medication (e.g., measured in mg/ml), the dosage rate of the medication (e.g., measured in mg/kg), and the patient's weight (e.g., measured in kg). The system 10 may advantageously be programmed with default values for the concentrations and dosage rates for each of the plurality of medications received in the system. Therefore, as one will readily appreciate, inputting the patient's weight with at least one of the weight adjustment keys 26 or 28 is all that is typically necessary in order for the system 10 to calculate a dosage amount for all medications to be administered. Additionally, the system 10 includes a weight readout display 24 that readily allows an emergency medical provider or other user to see the weight value entered into the system 10.

In an alternative embodiment, the device may have an age-related input to fine-tune dosages based on the age of a patient. Some medications or dosages that may be appropriate for an adult or adolescent may be inappropriate or dangerous for a child. The input (not shown) may be based on age (e.g., by year) or by age category (e.g., above or below 12 years of age). Similarly, the system may be programmed with Broselow tape color coding so that the practitioner has only to select the color corresponding to the length of the patient as defined by the Broselow tape system. Patient dosages corresponding to the selected color (and length range, and estimated weight range) are preprogrammed into the system.

In one embodiment, the system 10 may include complementary inject and abort keys 30 and 32, respectively. In one embodiment, an injection order is entered by pressing at least one of the medication selection keys 14 and an emergency medical provider can subsequently initiate the injection order by pressing the inject key 30. In another embodiment, an emergency medical provider or other user can initiate an inject command for at least one medication received in the system without first selecting medication(s) with the medication selection keys 14 (e.g., such a system may be programmed to inject a calculated amount of each medication). In either case, when the inject key 30 is pressed, the system 10 is programmed to dispense a dosage amount of at least one medication based on the concentration of the medication, the dosage rate, and the patient's weight. The abort key 32 performs the opposite function. The abort key 32 is configured to suspend an injection order or an in process dispensal of medication. For example, if the wrong medications are accidentally selected and/or the patient has an abnormal or unexpected response to the medication, an emergency medical provider can use the abort key 32 to suspend an injection order or in an process injection.

In one embodiment, the system 10 may include a bolus/flush key 34 configured to activate a bolus/flush mechanism. For example, if an emergency medical provider needs to flush a medication directly into a patient's heart or another organ, the bolus/flush mechanism will follow a medication with a so-called bolus of fluid sufficient to push the medication through the patient's circulatory system and into a desired organ. Also, the bolus/flush mechanisms may be used to flush the medication out of the fluid lines and other parts of the system 10 and into the patient.

In one embodiment, the system 10 may include at least one delivery tube 36. The delivery tube 36 is configured to transport medication from the one or more medication ampoules (e.g., ampoule 38*f*) received in the system 10 to a patient. In particular, the at least one delivery tube 36 is configured to transport the calculated dosage amounts of the one or more medications from the system 10 to a patient.

Figure 2B:
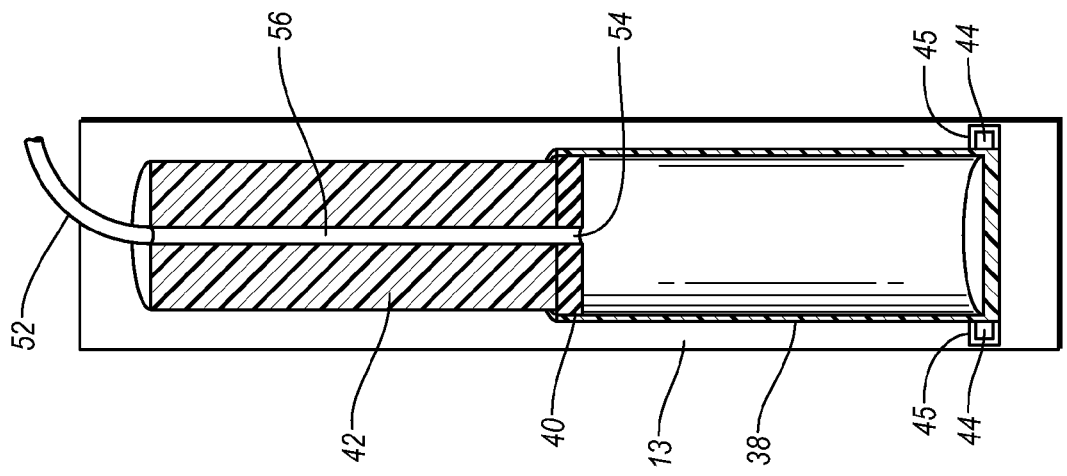
FIG. 2B illustrates a cross-sectional view of the piston pump depicted in FIG. 2A.
Figure 2A:
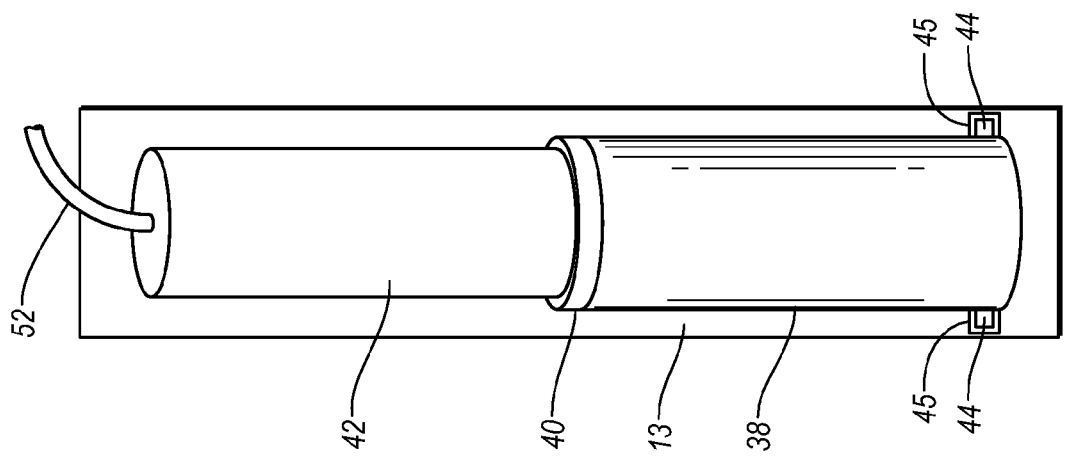
FIG. 2A illustrates a schematic view of a medication port including a medication ampoule and an embodiment of a piston pump for pumping medication out of a medication ampoule.

Focusing now on a medication port 13, FIGS. 2A and 2B depict an exemplary medication port 13 configured to receive a medication ampoule 38. FIG. 2A illustrates a schematic view of a medication port 13 including a medication ampoule 38 and an example of a piston pump 42 for pumping medication out of a medication ampoule 38. Of course, other pump systems known in the art may be employed.

In one embodiment, a medication ampoule 38 is received in a medication port 13 by snapping or sliding the ampoule onto the distal end of a piston 42. In one embodiment, the distal end of the piston 42 includes a plunger 40 comprised of rubber or a similar substance that creates a seal between the plunger 40 and the inner surface of the ampoule 38. As will be discussed more fully below, the piston 42 is configured to pump the medication solution out of the ampoule 38 when either the plunger 40 is pushed down into the ampoule 38 or when the ampoule is pushed up into the piston 42, causing the plunger 40 to slide distally within the ampoule 38.

In one embodiment, the ampoule 38 and the port 13 may include one or more safety means configured to insure that only one type of ampoule 38 and therefore one type of medication may be installed in a given port 13. In one embodiment, the safety means may be configured as a mechanical interlocking structure wherein each of the plurality of ports 13 are equipped with a specific arrangement of keyways, e.g., tabs and/or channel-shaped structures, and each type of ampoule 38 is equipped with a complementary arrangement of mechanical structures. When an ampoule 38 is installed in a port 13 to which it corresponds, the safety interlocking structures of the ampoule mate with the complementary structures of the port 13. As such, a given ampoule cannot be installed in a medication port to which it does not correspond. For example, as depicted in FIGS. 2A & 2B, the safety means may comprise a plurality of tab structures 44 or annular or semi-annular rings that fit into a complementary channel or channels 45 in the port 13.

In another embodiment, the safety means may include a color matching system (not shown) wherein each port 13*a*-13*f* is designated by a specific color and each type of medication ampoule 38*a*-38*f* is designated with a specific color that matches to port to which it corresponds.

In another embodiment, the safety means may include a name matching system wherein the name of the medication corresponding to a port is clearly printed on both the port 13*a*-13*f* and/or on the corresponding door 12*a*-12*f* on the medication ampoule 38*a*-38*f*.

FIG. 2B illustrates a cross-sectional view of the medication port 13 including a medication ampoule 38 as depicted in FIG. 2A. As perhaps best seen in FIG. 2B, the medication solution is forced through a hole 54 in the distal face of the plunger 40 and through a central channel 56 in the piston 42 when the piston 42 is pushed down into the ampoule 38 or when the ampoule 38 is pushed up towards the piston 42. In one a embodiment, a plurality of distribution tubes 52 (FIG. 3) connect to the dispensing tube 36 whereby the medication is carried to a patient.

Figure 3:
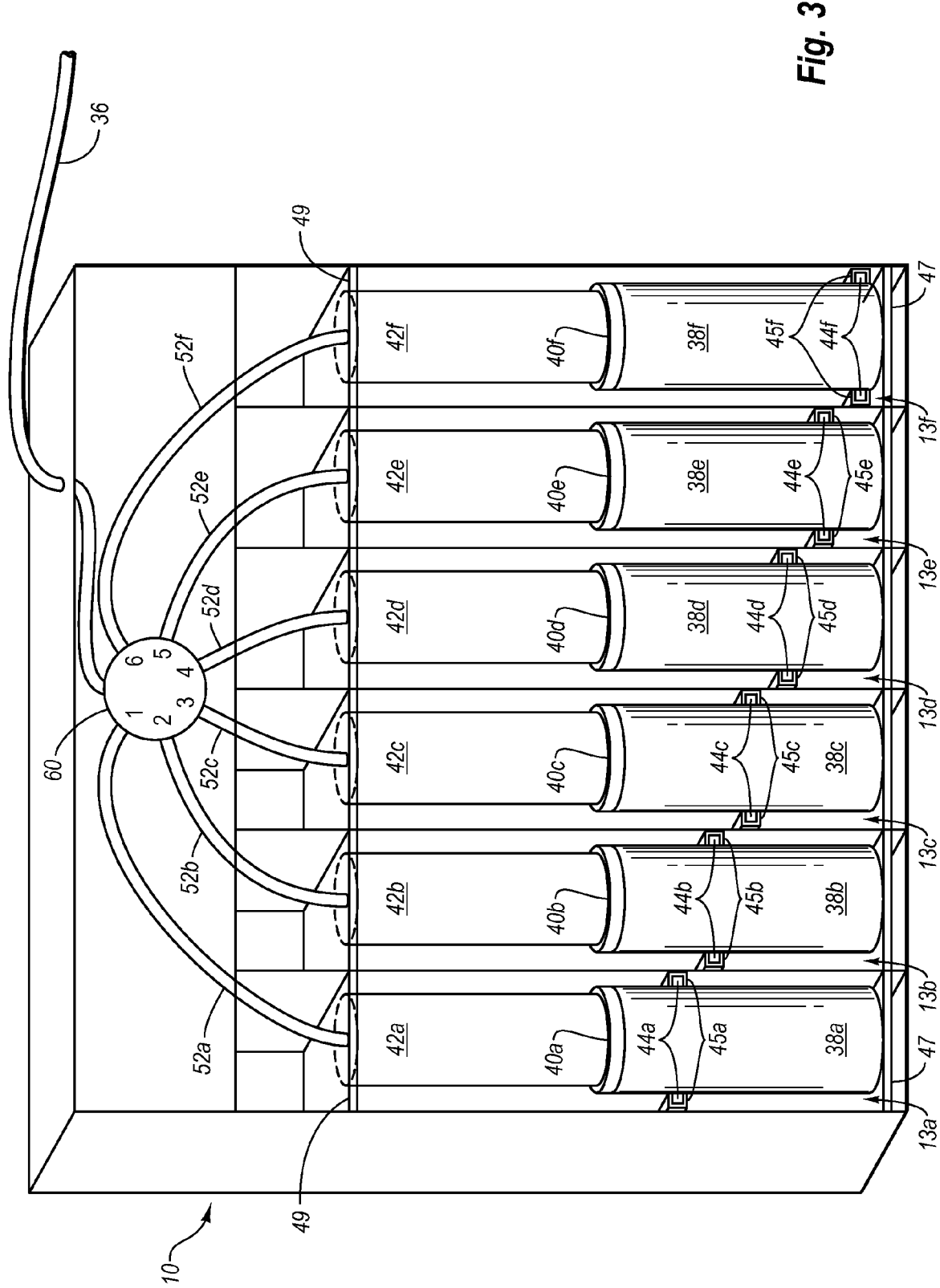
FIG. 3 illustrates a cut-away view of an embodiment of a multi-medication pump injection system showing the interior of the system.

FIG. 3 illustrates a view of an exemplary of an emergency medication pump system 10 with the top cover of the housing removed to show one example of how the various medications may be delivered into tube 36. Other configurations will be apparent to those skilled in the art. In the illustrated embodiment, the plurality of pump mechanisms 42*a*-42*f* may include a plurality of distribution tubes 52*a*-52*f* configured to convey medications pumped from the medication ampoules 38*a*-38*f* to a switching valve 60. In turn, the switching valve 60 may be connected to the distal end of a dispensing tube 36, which transports the medication(s) to a patient.

In an emergency medical situation the chances of giving the wrong medication to a patient are elevated because of the often chaotic environment created by an emergency. Therefore, the illustrated system 10 includes safety means ensure that a medication ampoule (e.g., 38*a*) is only inserted into a medication port to which it corresponds (i.e., 13*a*).

As illustrated, the safety means may include a system of mechanical interlocking structures wherein each of the plurality of ports (e.g., 13*a*) are equipped with a portion of the specific arrangement interlocking structures, e.g., tabs and/or channel-shaped grooves or other recess structures (e.g., 45*a*), and each type of ampoule (e.g., 38*a*) is equipped with a complementary and specific arrangement of interlocking structures (e.g., tabs, protrusions, or annular/semi-annular rings 44*a*). FIG. 3 depicts an example of how each medication port is provided with an arrangement of interlocking mechanical structures (e.g., 45*a*-45*f*) that is different from the arrangement found in neighboring ports. Likewise, each type of ampoule is provided with a complementary arrangement of mechanical structures (e.g., 44*a*-44*f*) where each is different from the arrangement of other ampoule types. In other words, an ampoule containing Etomidate, for example, is provided with a specific arrangement of mechanical structures that is complementary only to a port intended for Etomidate, while an ampoule containing Propofol, for example, is provided with a specific and different arrangement of mechanical structures that that is complementary only to a port intended for Propofol.

For example, when ampoule 38*a* is installed in port 13*a*, the mechanical protrusions 44*a* of ampoule 38*a* mate with the recesses 45*a* port 13*a*. As will be appreciated from this example, ampoule 38*a* cannot be inserted into a medication port to which it does not correspond (i.e., any of the ports 13*b*-13*f*) because the mechanical protrusions 44*a* of ampoule 38*a* will not mate with the receiving recesses of those ports. That is, the arrangement of mechanical interlock structures in each port is incompatible with any ampoule except that type intended for the particular port. Additionally, the system may be equipped with a pair of stops 47 and 49 that further prevent an ampoule from being inserted in a port to which it does not correspond. In short, the stops 47, 49 prevent an ampoule/pump assembly from being pushed up or down within the housing, thereby preventing the mechanical structures on an ampoule from being fit into a higher or lower set of interlocking mechanical structures intended for another ampoule type.

Another example of safety means may include a color matching system wherein each of the medication ports 13*a*-13*f* is designated with a specific color and each medication ampoule 38*a*-38*f* is also designated with a specific color. When an ampoule (e.g., ampoule 38*a*) is received in the port to which it corresponds (e.g., port 13*a*), the user can visually confirm that the color of the port is the same as the color of the ampoule (i.e., the colors match). This system also facilitates quick and easy replacement of ampoules within the device, as the practitioner has only to identify like colors and insert the ampoules in like colored ports.

In another example, safety means may include a labeling system wherein the name of the medication corresponding to a port (e.g., 13a) is clearly printed (preferably in large, clear letters) on both the port (e.g., 13a) and on the medication ampoule corresponding to the port (e.g., 38a). The label may also include a shape or other symbol which designates a particular port and its corresponding medication. When an ampoule (e.g., 38a) is received in the port to which it corresponds (e.g., 13a), the names will be identical. If, on the other hand, there is an attempt to install an ampoule (e.g., 38a) in a port to which it does not correspond, the names will not match. Such a labeling system has an additional advantage in that it allows an emergency medical provider to quickly ascertain which medications are installed in the system 10 and in which port 13a-13f each is received.

One will appreciate, of course, that the system 10 may preferably include more than one of the above described safety means. For example, a preferred embodiment may include a mechanical interlock system in addition to a color matching system and/or a labeling system. A particularly preferred embodiment may include all three (i.e., a mechanical interlock system, a color matching system, and a labeling system). In other words, it may be advantageous for the safety means included with the system to be multiply redundant. Multiple redundancies are preferable because the safety means are intended to ensure that each ampoule is only installed in a port to which it corresponds, which in turn is intended to ensure that a patient is not accidentally dosed with the wrong medication.

Figure 4:
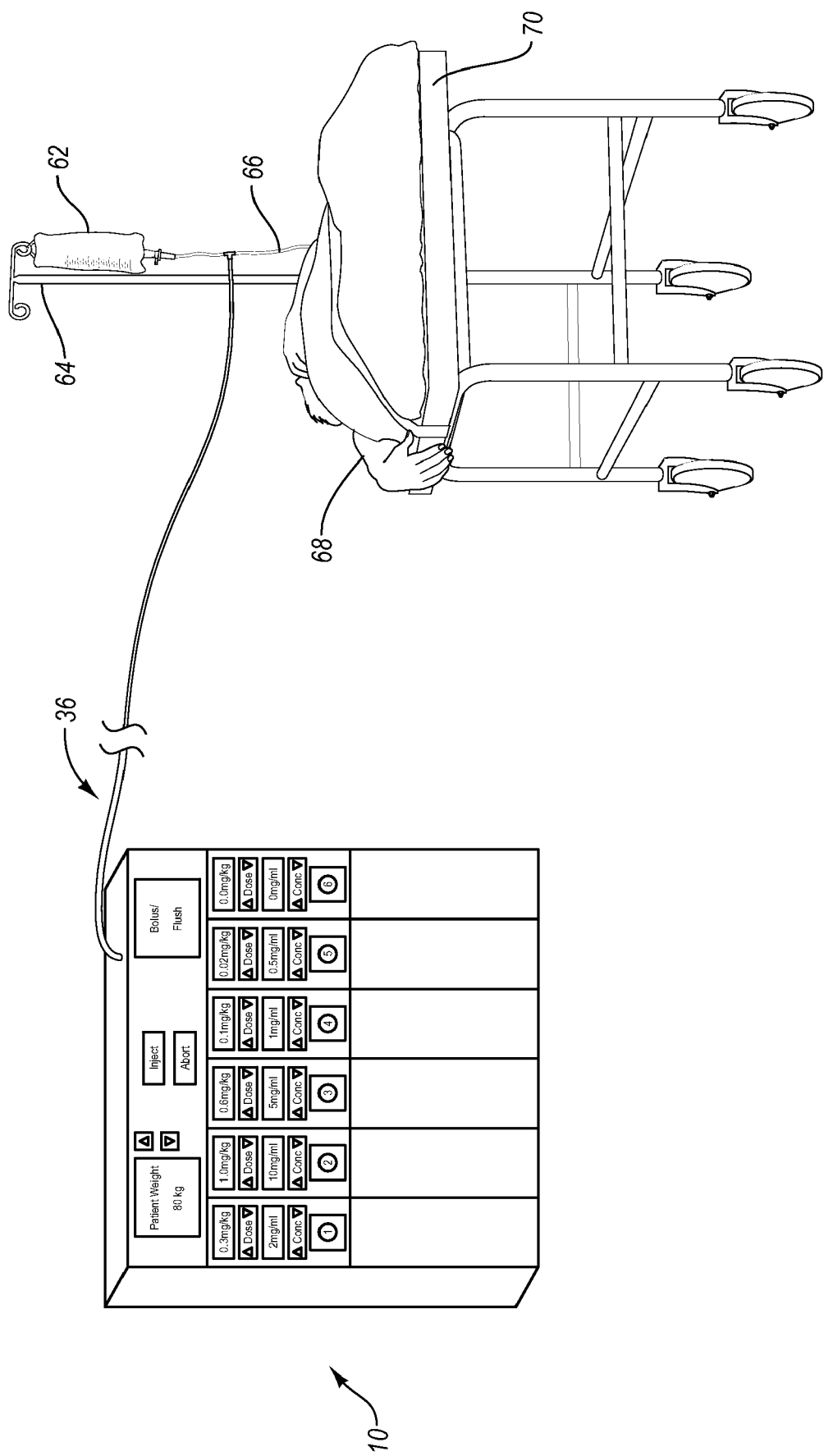
FIG. 4 illustrates a schematic view of an embodiment of a multi-medication pump injection system as it would be attached to a patient in an emergency setting.

FIG. 4 illustrates a schematic view of an embodiment of an emergency medication pump system 10 attached to a patient 68. When a patient 68 arrives in an emergency department or when a patient 68 is contacted in the field by emergency medical technicians, the emergency medical personnel will rapidly assess the patient's medical condition, and begin administering IV fluids 62. In one embodiment, the system 10 is attached directly to the patient's IV line 66. After attaching the system 10 to the patient's IV line 66, the system 10 can be used to accurately administer one or more medications to the patient. As was discussed more fully above, the emergency medical provider can administer one or more medications to the patient in rapid sequence by selecting at least one medication, entering the patient's weight and/or the patient's Broselow color (and/or length), and pressing the inject key. The medication(s) is then carried to the patient's IV line 66 via delivery tube 36; the IV line 66 then carries the medication into the patient's circulatory system along with the IV fluid.

It is important to remember that a system like the one described herein (e.g., system 10) frees emergency medical personnel from having to locate each medication and perform a separate calculation in order to arrive at a correct dosage for each and every medication given to a patient. In an emergency situation, time is of the essence and these locating and calculating steps cost valuable time. The system is speedy and simple. IV access and a patient's weight may be all that is required to accurately and immediately administer medications. Risk of error is greatly reduced, as the accuracy of the dose is assured by the system. There is virtually no chance of mix-up of syringes that are otherwise identical in appearance. Safety is optimized by automatically calculating and delivering the appropriate dose of medication. Errors caused by miscalculation or miscommunication in a loud and chaotic trauma bay are reduced or eliminated. Safety and accuracy in dealing with pediatric patients is particularly paramount. As noted, larger pediatric hospitals often require that the calculations and drawing up of medications be performed by a pharmacist. Automation of the process by the inventive system allows any facility, regardless of size or resources to provide safe, accurate medication dosing to every patient. Safety is further optimized by the medication ampoule and port configurations described above in which placing the wrong medication ampoule in any given port would be virtually impossible.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A multi-medication pump injection system for use in an emergency medical situation in which medications are administered to a patient in rapid succession and in proper sequence, comprising: a compact, portable housing comprising a plurality of medication ports, wherein each port is configured to receive a corresponding ampoule containing a corresponding medication; at least one pump disposed on or within the housing for dispensing a dosage amount of medication from one or more ampoules received within the housing during use; safety means for ensuring that each ampoule is only capable of being installed in a port to which the ampoule corresponds; at least one delivery tube having a distal end and at least one proximal end, wherein the at least one proximal end is configured to receive one or more medications dispensed from one or more ampoules and deliver the one or more medications to the distal end for delivery to a patient; and a microprocessor module that is programmable in order to cause the system to deliver a plurality of medications in rapid succession and in a predetermined sequence to a patient and also to deliver a predetermined dosage of one or more medications based on input of a patient's weight and/or length.

2. A multi-medication pump system as recited in claim 1, wherein the system is programmed to deliver a plurality of medications intravenously to a patient upon input of only a patient's weight into the microprocessor module.

3. A multi-medication pump system as recited in claim 2, further comprising an input interface by which a patient's weight can be entered into the microprocessor module.

4. A multi-medication pump system as recited in claim 1, further comprising an input interface comprising a plurality of medication selection keys corresponding to and disposed adjacent the plurality of medication ports and wherein the order in which the keys are selected determines a sequence of administration of a plurality of corresponding medications.

5. A multi-medication pump system as recited in claim 1, further comprising an input interface comprising an inject key and an abort key, and wherein one or more medications are administered to a patient in response to selection of the inject key, and wherein selection of the inject key can be canceled by selection of the abort key.

6. A multi-medication pump system as recited in claim 1, wherein one of the ports is configured to receive a bolus/flush ampoule, such that the system is configured to flush the medication out of the delivery tube and into a patient with a bolus of fluid.

7. A multi-medication pump system as recited in claim 1, wherein the system is programmed with a plurality of default values, comprising:
   a default concentration value for each of the plurality of medications corresponding to each of the medication ports; and
   a default dosage rate for each of the plurality of medications corresponding to each of the medication ports.

8. A multi-medication pump system as recited in claim 7, wherein the system further comprises an input interface comprising a plurality of concentration adjustment keys corresponding to and disposed adjacent the plurality of medication ports, and wherein each concentration adjustment key is configured to override a corresponding default concentration value of a medication in a corresponding medication port.

9. A multi-medication pump system as recited in claim 7, wherein the system further comprises an input interface comprising a plurality of dosage rate adjustment keys corresponding to and disposed adjacent the plurality of medication ports, and wherein each dosage rate adjustment key is configured to override a corresponding default dosage rate of a medication in a corresponding medication port.

10. A multi-medication pump system as recited in claim 1, wherein the safety means comprises a color-coding system wherein each port comprises an ampoule selection color corresponding to a color of a corresponding ampoule for receipt into the port.

11. A multi-medication pump system as recited in claim 1, wherein the safety means comprise a mechanical interlock system wherein each of the medication ports is configured with a first portion of a unique arrangement of mechanical interlock structures configured to mate with a second complementary portion of the unique mechanical structures contained in a corresponding ampoule to be received within the port.

12. A multi-medication pump system as recited in claim 11, wherein the mechanical interlock structures comprise recesses and/or protrusions.

13. A multi-medication pump system as recited in claim 1, wherein the safety means comprise a label system wherein each port comprises a name printed thereon corresponding to an ampoule of the same name.

14. A multi-medication pump system as recited in claim 1, further comprising a plurality of ampoules containing medication.

15. A multi-medication pump system as recited in claim 14, wherein the safety means comprises:
  a mechanical interlock system wherein each of the medication ports is configured with a first portion of a unique arrangement of mechanical interlock structures, and each ampoule is configured with a second complementary portion of the unique mechanical structures such that each ampoule is configured to be received within only one corresponding port; and
  at least one of:
    a color-coding system wherein each ampoule comprises a unique color and each port comprises the same color as the ampoule corresponding to that port so that the color of the ampoule is identical to the color of the corresponding port; or
    a label system wherein each port and each corresponding ampoule comprise an identical name printed on both the port and the corresponding ampoule.

16. A multi-medication pump system as recited in claim 1, wherein the at least one pump comprises a piston pump configured to force the medication out of a corresponding ampoule and into a proximal end of a delivery tube for delivery to a patient.

17. A multi-medication pump system as recited in claim 1, the system including a single delivery tube through which a plurality of medications are deliverable to a patient during use, the system further comprising a switching valve disposed between the at least one pump and the single delivery tube.

18. A multi-medication pump system as recited in claim 1, wherein the system occupies a volume not greater than about 18 dm$^3$ and wherein the medication ports are sized and configured so that a plurality of medication ampoules received within the medication ports can be enclosed within and protected by the housing during use.

19. A multi-medication pump system as recited in claim 1, wherein the system occupies volume not greater than about 9 dm$^3$.

20. A multi-medication pump system as recited in claim 1, wherein the system occupies volume not greater than about 6 dm$^3$.

21. A multi-medication pump system as recited in claim 1, wherein the system has a weight between about 1 kg and about 5 kg.

22. A multi-medication pump system as recited in claim 1, wherein the system has a weight between about 2 kg and about 4 kg.

23. A multi-medication pump system as recited in claim 1, wherein the system has a weight not greater than about 3 kg.

24. A multi-medication pump injection system for use in an emergency medical situation in which medications are rapidly administered to a patient in rapid succession and in proper sequence, comprising:
  a compact, portable housing having a weight not greater than about 3 kg and occupying a volume not greater than about 6 dm$^3$, the housing comprising a plurality of medication ports, wherein each port is configured to receive a corresponding ampoule containing a corresponding medication, the medication ports being sized and configured so that a plurality of medication ampoules received within the medication ports are enclosed within and protected by the housing during use;
  safety means for ensuring that each of a plurality of ampoules is only capable of being installed in a port to which the ampoule corresponds;
  a microprocessor module that is programmable in order to cause the system to rapidly deliver a plurality of medications in rapid succession and in a predetermined sequence to a patient during an emergency medical situation;
  at least one pump disposed on or within the housing for dispensing a dosage amount of medication from one or more of the plurality of ampoules received within the housing; and
  a single delivery tube having a distal end and at least one proximal end, wherein the at least one proximal end is configured to receive a plurality of medications dispensed from a plurality of ampoules and deliver the medications to the distal end for delivery to a patient.

25. A multi-medication pump injection system for use in an emergency medical situation in which medications are administered to a patient in rapid succession and in proper sequence, comprising:
  a compact, portable housing comprising a plurality of medication ports, wherein each port is configured to receive a corresponding ampoule containing a corresponding medication;
  a mechanical interlock system wherein each of the medication ports is configured with a first portion of a unique arrangement of mechanical interlock structures, and each of a plurality of ampoules is configured with a second complementary portion of the unique mechanical structures such that each ampoule is configured to be only capable of being received within only one corresponding port of the portable housing;

at least one pump disposed on or within the housing for dispensing a dosage amount of medication from one or more of the plurality of ampoules received within the housing; and at least one delivery tube having a distal end and at least one proximal end, wherein the at least one proximal end is configured to receive one or more medications dispensed from a plurality of ampoules and deliver the one or more medications to the distal end for delivery to a patient.

* * * * *

UNITED STATES PATENT AND TRADEMARK OFFICE
CERTIFICATE OF CORRECTION

Page 1 of 2

PATENT NO. : 7,815,605 B2
APPLICATION NO. : 11/946740
DATED : October 19, 2010
INVENTOR(S) : Souter It is certified that error appears in the above-identified patent and that said Letters Patent is hereby corrected as shown below:

Drawings
Sheet 4, replace Figure 4 with the figure depicted below, wherein the reference numerals "64" and "70" have been removed

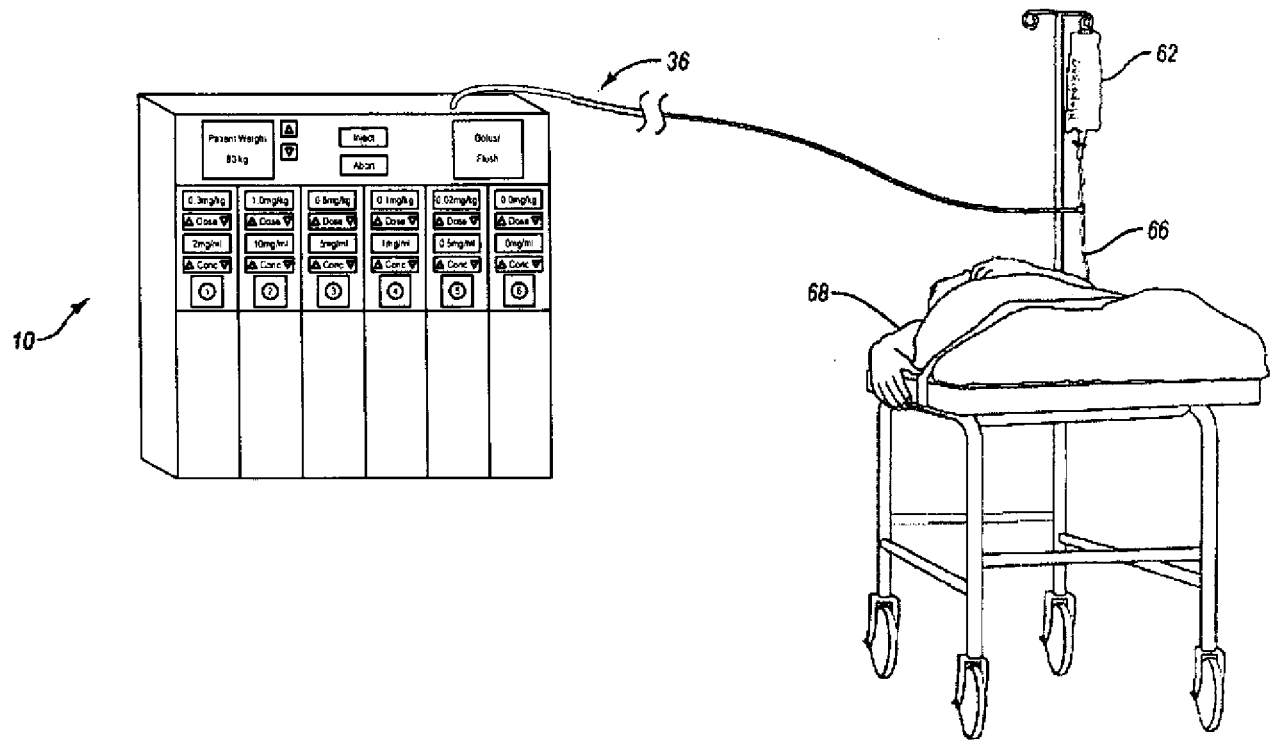

Fig. 4

Column 3
Line 64, change "patient's" to --patients--

Column 7
Line 2, change "a average" to --an average--

Signed and Sealed this
Eighteenth Day of September, 2012

David J. Kappos
*Director of the United States Patent and Trademark Office*

CERTIFICATE OF CORRECTION (continued)
U.S. Pat. No. 7,815,605 B2

Column 10
Line 63, change "in an" to --an in--

Column 11
Line 4, change "mechanisms" to --mechanism--
Line 55, change "to port" to --to the port--

Column 12
Line 1, change "one a embodiment" to --one embodiment--
Line 4, change "exemplary" to --example--
Line 18, change "means ensure" to --means to ensure--
Line 45, change "45*a* port 13*a*" to --45*a* of port 13*a*--

Column 15
Line 21, change "comprise" to --comprises--
Line 32, change "comprise" to --comprises--